United States Patent [19]

Takeda et al.

[11] 4,158,009
[45] Jun. 12, 1979

[54] PROCESS FOR PREPARING 1,5-DINITROANTHRAQUINONE

[75] Inventors: Yoshiyuki Takeda; Shinichiro Koga, both of Kitakyusyu; Yutaka Fukuda, Nakama, all of Japan

[73] Assignee: Mitsubishi Chemical Industries Ltd., Tokyo, Japan

[21] Appl. No.: 831,223

[22] Filed: Sep. 7, 1977

[30] Foreign Application Priority Data

Sep. 13, 1976 [JP] Japan .................................. 51-109669

[51] Int. Cl.² .............................................. C07C 49/68
[52] U.S. Cl. ............................................................ 260/369
[58] Field of Search ............................................. 260/369

[56] References Cited

U.S. PATENT DOCUMENTS

| 3,818,052 | 6/1974 | Hohmann et al. | 260/369 |
| 3,906,011 | 9/1975 | Auge et al. | 260/369 |
| 3,963,761 | 6/1976 | Vogel | 260/369 |
| 3,963,762 | 6/1976 | Hohmann | 260/369 |

OTHER PUBLICATIONS

*Chemical Abstracts,* vol. 26, 1932, p. 1278, Hefti, E., "Dinitro-anthraquinones".
*Chemical Abstracts,* vol. 83, No. 9, Jan. 16, 1975, p. 636, abstract No. 78970w, "1,5-dinitroanthraquinone separation from its isomers".

*Primary Examiner*—Thomas Waltz
*Assistant Examiner*—Raymond K. Covington
*Attorney, Agent, or Firm*—Lane, Aitken & Ziems

[57] ABSTRACT

A mixture of various dinitroanthraquinone isomers prepared from anthraquinone by mixed acid nitration is subjected to a suspension treatment at a temperature above 50° C. with a mixed acid of a content satisfying the following three equations and then the crystals of 1,5-dinitroanthraquinone are separated:

$$y \leq -2x + 230,$$

$$50 \leq y \leq 75 \text{ and}$$

$$y \leq -2x + 110,$$

wherein $$x = \frac{\text{nitric acid (mol.)}}{\text{dinitroanthraquinone (mol.)}} \text{ and}$$

$$y = \frac{\text{nitric acid (weight)}}{\text{nitric acid (weight) + sulfuric acid (weight)}} \times 100$$

1,5-dinitroanthraquinone of a high purity can be obtained with ease.

9 Claims, 2 Drawing Figures

PROCESS FOR PREPARING 1,5-DINITROANTHRAQUINONE

BACKGROUND OF THE INVENTION

This invention relates to a process for producing 1,5-dinitroanthraquinone and, in particular, to a process for separating 1,5-dinitroanthraquinone of a high purity from a mixture containing various dinitroanthraquinone isomers prepared from anthraqinone by nitrating the same with a mixed acid (a mixture of nitric acid and sulfuric acid).

Dinitroanthraquinones have been used widely, in general, as an intermediates for the production of dyes or the like and, among all, 1,5-dinitroanthraquinone is important as an intermediate for blue color dyes of a high fastness to sublimation. 1,5-dinitroanthraquinone is generally produced by nitrating anthraquinone with a mixed acid but the 1,5-dinitroanthraquinone thus prepared contains, in most cases, 1,8-dinitroanthraquinone, 1,6-dinitroanthraquinone, 2,6-dinitroanthraquinone and the like, that is, it is obtained as a mixture of various isomers.

Isolation of pure 1,5-dinitroanthraquinone from the above isomer mixture has heretofore required a complicated process, for example, heating the mixture together with 100% by weight sulfuric acid to isolate less soluble 1,5-dinitroanthraquinone from other isomers and then further recrystallizing the same from an appropriate solvent.

SUMMARY OF THE INVENTION

In view of the foregoing, we have made a study on a process for separating 1,5-dinitroanthraquinone from a mixture of various dinitroanthraquinone isomers and, as a result, accomplished this invention based on the finding that 1,5-dinitroanthraquinone can be prepared with ease by subjecting the above isomer mixture to a suspension treatment in a specified suspending medium at a specified temperature. Accordingly, the object of this invention is to provide an industrially advantageous process for preparing 1,5-dinitroanthraquinone of a high purity by separating it from a mixture of various dinitroanthraquinone isomers prepared through nitration of anthraquinone with a mixed acid, and the object can be attained with ease by subjecting a mixture of various dinitroanthraquinone isomers obtained from anthraquinone by the nitration reaction with nitric acid in the presence of a mixed acid consisting sulfuric acid and nitric acid to a suspension treatment at a temperature from 50° to 90° C. in a mixed acid consisting of sulfuric acid and nitric acid in a proportion satisfying the following three equations (1) to (3):

$$y \leq -2x + 230 \quad (1),$$

$$50 \leq y \leq 75 \quad (2) \text{ and}$$

$$y \geq -2x + 110 \quad (3),$$

wherein $$x \text{ represents } \frac{\text{nitric acid (mol.)}}{\text{dinitroanthraquinone (mol.)}}$$

$$y \text{ represents } \frac{\text{nitric acid (weight)}}{\text{nitric acid (weight)} + \text{sulfuric acid (weight)}} \times 100$$

and then isolating the crystals of 1,5-dinitroanthraquinone therefrom.

$$x : \frac{\text{nitric acid (mol.)}}{\text{dinitroanthraquinone (mol.)}}$$

$$y : \frac{\text{nitric acid (weight)}}{\text{nitric acid (weight)} + \text{sulfuric acid (weight)}} \times 100$$

Figure 2:
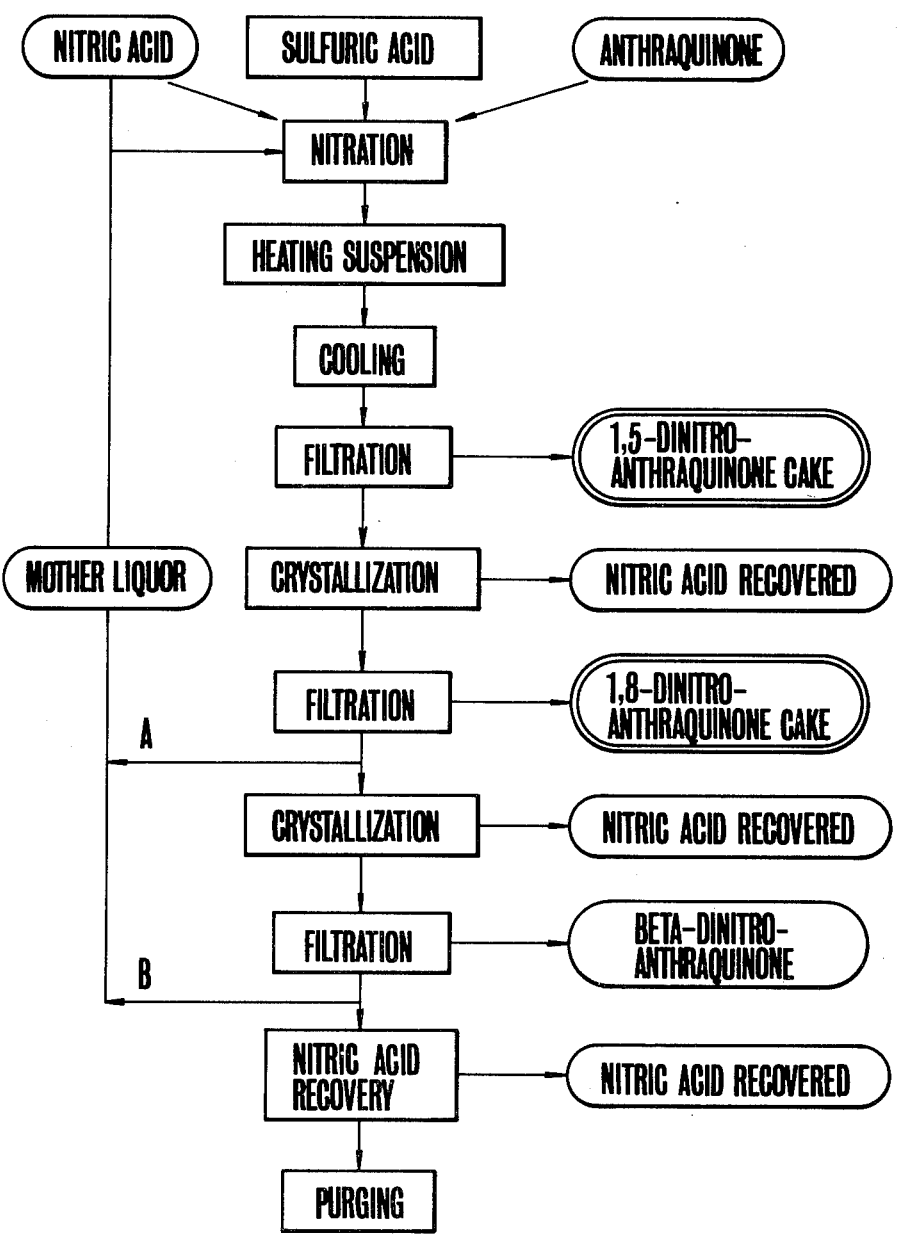

FIG. 2 is a block diagram showing one embodiment of this invention.

DESCRIPTION OF PREFERRED EMBODIMENTS

A mixture of various dinitroanthraquinone isomers obtained from anthraquinone by the mixed acid nitration is used as a starting mixture in this invention and the composition thereof is, for example, as follows:

Nitric acid component: 45–55% by weight
Sulfuric acid component: 40–45% by weight
Nitroanthraquinones: 3–10% by weight
which usually consists of
  1,5-dinitroanthraquinone: 35–42% by weight
  1,8-dinitroanthraquinone: 4–38% by weight
  other dinitroanthraquinone isomers: 9–27% by weight In this invention, the above mixture is suspended in a mixed acid of a specified composition and a specified amount to separate 1,5-dinitroanthraquinone therefrom at a high yield. In the suspension treatment, the starting mixture may be once removed from the mixed acid used for the nitration, but it is usually desired to conduct the suspension treatment in the mixed acid slurry as it is, or after optionally adjusting the amount of the mixed acid as required. The composition and the amount of the mixed acid used for the suspension treatment have a correlation between each other and they should be adjusted with respect to the amount of the dinitroanthraquinone in the starting mixture so as to satisfy the foregoing equations (1)–(3) and, more desirably, the following three equations (4)–(6):

$$y \leq -2x + 210 \quad (4),$$

$$52 \leq y \leq 75 \quad (5) \text{ and}$$

$$y \geq -2x + 130 \quad (6),$$

wherein x and y have the same meanings as in the above equations (1)–(3). The equation (5) may, further desirably, be $$55 \leq y \leq 65. \quad (5')$$

Figure 1:
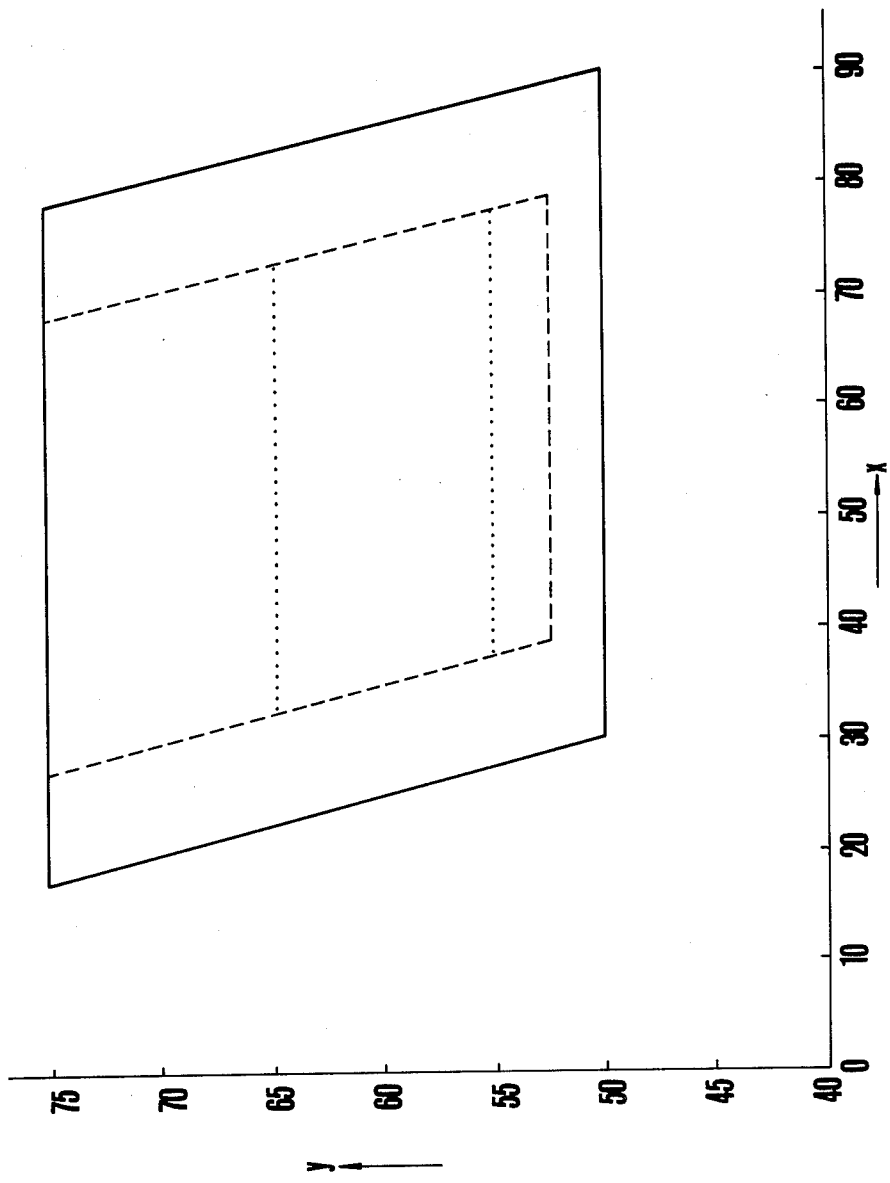
FIG. 1 is a figure showing the relation between the amounts of nitric acid, sulfuric acid and anthraquinone, wherein the region confined by a solid line shows a range to which this invention is applicable. In the figure.

FIG. 1 of the drawings shows a region defined by the foregoing equations (1)–(3) (the area confined by a solid line) and regions defined by the foregoing equations (4)–(6) and (4), (5') and (6) respectively (the areas confined by a broken line and a dotted line). In the drawing, y and x are taken along an ordinate and an abscissa, respectively.

If the relations among the above factors do not satisfy the foregoing equations, various disadvantages are brought about as follows:

$y > -2x + 230$: Amount of nitric acid is in excess, where the amount of 1,5-dinitroanthraquinone dissolved therein is increased to lower the yield of 1,5-dinitroanthraquinone, as well as lower the slurry concentration in the separation process described hereinafter thus increase the load applied on the separator.

$y < -2x + 110$: Amount of nitric acid is insufficient, where the viscosity of the slurry is increased to necessitate a higher separation temperature above 90° C. for the smooth separation, which results in a violent corrosive effect of the mixed acid. This imposes a strict restriction on the choice of the separator material and a separator of costly material has to be used.

$y < 50$: Nitric acid ratio in the mixed acid is too low, where leaching of dinitroanthraquinone isomers soluble in nitric acid, including 1,8-dinitroanthraquinone, is not sufficient thus failing to obtain 1,5-dinitroanthraquinone of a high purity.

$y > 75$: Nitric acid ratio in the mixed acid is too high, which is undesirable from an economical point of view.

While the effect of the suspension treatment is not sufficient at a temperature below 50° C. and it increases with the rise in temperature, too high a temperature is undesired since it increases the amount of nitrogen oxides (NOx) and produces such impurities as nitromethanes and oxides of dinitroanthraquinones. The temperature for the suspension treatment is, therefore, between about 50° and about 90° C. and, more preferably, between 55° and about 85° C. Time required for the suspension treatment can be shortened as the treating temperature goes higher and is, for example, between about 3–15 hours for 50° C., 1–10 hours for 70° C. and 0.5–7 hours for 80° C.

1,5-Dinitroanthraquinone which is less soluble in the mixed acid is separated from the mixed acid slurry after the suspension treatment. The mixed acid slurry is, desirably, cooled below 70° C., preferably to 30°–60° C., for example 35°–45° C. prior to the separation since it results in coarser grains of 1,5-dinitroanthraquinone to facilitate the separation. The cooling of the mixed acid slurry may be effected either in a one-stage gradual cooling or in a multi-stage cooling system.

The separation of 1,5-dinitroanthraquinone is conducted at a temperature between about 30° and about 90° C. and, preferably, between about 35° and about 85° C. At a temperature beyond the above range, the corrosive effect of the mixed acid becomes violent presenting a problem in the choice of the material of the separator, and the amounts of nitrogen oxides and the like are increased to make the separation difficult.

The purity of 1,5-dinitroanthraquinone may depend on the temperature for the separation and it is hence desired to determine the foregoing factors x and y while taking the above temperature into consideration. Preferred specific relations between the separation temperature and x for producing 1,5-dinitroanthraquinone of a purity more than 90% under the conditions of $y = 60$ or 70 are, for example, as below:

| separation temperature ($y = 60$) | x |
| --- | --- |
| 50° C. | not less than 40 |
| 80° C. | not less than 35 |
| separation temperature ($y = 70$) | |
| 40° C. | not less than 35 |
| 70° C. | not less than 25 |

1,5-Dinotroanthraquinone prepared by the separation is subjected to water washing and drying in a well-known manner and can be used as an intermediate for disperse dyes. Meanwhile, other dinitroanthraquinones mainly consisting of 1,8-dinitroanthraquinone can be recovered by distilling off nitric acid from the mixed acid mother liquor.

The separation process of this invention is, desirably, effected in combination with the mixed acid nitration of anthraquinone, by which 1,5-dinitroanthraquinone of a high purity can be recovered directly from the reaction system at a high yield. In this case, it is desired to determine the composition and the amount of the mixed acid to be used in the nitration reaction so that the composition and the amount of the mixed acid after the reaction can satisfy the foregoing equations (1)–(3) considering the amount of the nitric acid to be consumed in the reaction. Nitration under the conditions of y being between 30 and 80 and x being not less than 4, preferably, not less than 10 is desired since the composition and the amount of the mixed acid after the reaction can satisfy the equations (1)–(3) above described with no substantial adjustment therefor.

It is particularly preferred in this invention to effect the nitration by adding 1 mol. anthraquinone to the mixed acid containing more than 35 mol. nitric acid content for a period within two hours, whereby 1,5-dinitroanthraquinone of a high purity can be obtained.

The addition time means the time for the addition of anthraquinone in a batchwise reaction and means the residence time of the reactant solution in the reaction vessel in a continuous reaction. If the addition takes more than two hours, it is then difficult to produce 1,5-dinitroanthraquinone of a purity higher than 90%. Although the reasons therefor are not clear at present, it is supposed that the crude crystals precipitated out by the reaction under such a condition have a dense crystal structure and make it difficult to dissolve out impurities occluded therein upon suspension treatment with heating.

While on the other hand, too short addition times are also undesired, because the nitration of anthraquinone is so exothermic that the quantity of heat generated per unit time becomes so enormous as to necessitate the use of a heat exchanger of a large capacity. An addition time more than 0.1 hour, preferably, between about 0.2 and 1 hour is therefore desired.

The portionwise addition of anthraquinone may be effected continuously at a certain addition rate or effected intermittently. Specifically, it is desired to add a certain amount of anthraquinone to the mixed acid while stirring within a predetermined period of time at a constant rate.

The composition and the amount of the mixed acid after the completion of the nitration reaction can be adjusted by adding sulfuric acid or nitric acid to or distilling off nitric acid from the reaction system.

While the nitration reaction is usually effected between about −20° and 100° C., the contents of 1,5-dinitroanthraquinone and 1,8-dinitroanthraquinone in the dinitroanthraquinones tend to increase in a temperature range of −20° and 40° C. and the grain size of the resulted 1,5-dinitroanthraquinone tends to increase at a temperature 20° C. or more to facilitate the separation after the suspension treatment. The temperature for the nitration reaction may therefore be chosen properly considering the above factors.

As apparent from the foregoing description, high purity 1,5-dinitroanthraquinone is made available in accordance with the present invention by the suspension treatment of the mixture containing the various isomers of dinitroanthraquinone obtained by nitration reaction of anthraquinone with the mixed acid. The mother liquor can be reused for nitration reaction of anthraquinone after the separation of 1,8-dinitroanthraquinone or, 1,8-dinitroanthraquinone and β-dinitroanthraquinone (route A and route B, respectively in FIG. 2). Accordingly, fairly large crystals of 1,5-dinitroanthraquinone can be obtained so that the load of the filter is markedly decreased. Further, it is possible to eliminate the amount of sulfuric acid to be discarded from the production process and to effectively recover the various dinitroanthraquinone isomers in the waste sulfuric acid.

In the case where the mother liquor is reused after the separation of the aforesaid β-dinitroanthraquinone (route B in FIG. 2), the elimination of the amount of the waste acid is most effective.

As detailed above, the process of this invention provides a great industrial advantage since 1,5-dinitroanthraquinone of a high purity can easily be separated from a mixture containing various dinitroanthraquinone isomers by subjecting the mixture to a suspension treatment using a specified suspending medium at a specified temperature.

This invention will now be described more specifically by way of examples thereof but it should be understood that this invention is no way limited to such examples. In the examples, all "%" means % by weight.

EXAMPLES 1–7

These examples were conducted for demonstrating the production of 1,5-dinitroanthraquinone of a high purity by the suspension treatment with heating using, in each run, a specified amount of mixed acid in a once-through manner. The conditions and the results thereof are shown in Table 1.

Anthraquinone was added at a specified temperature and over a specified period of time to a mixed acid consisting of specified amounts of 98% nitric acid and 98% sulfuric acid with stirring, and stirring is further continued for a specified period of time. The resultant slurry was heated to a specified temperature and suspended over a specified period of time while stirring. The slurry was then cooled to a specified temperature to crystallize 1,5-dinitro isomer, which was thereafter filtered out and washed with 70% nitric acid to remove the mixed acid mother liquor. Then, 1,5-dinitro isomer cake was obtained after water washing and drying.

Analysis of the cake composition was performed by means of high speed liquid chromatography.

EXAMPLE 8

In this example, an additional amount of the mixed acid was supplemented to the slurry resulting from the nitration of anthraquinone to prepare a slurry containing a specified amount of mixed acid, which was subjected to the suspension treatment with heating.

208 g of anthraquinone was added to a mixed acid consisting of 984 g of 98% nitric acid and 1400 g of 98% sulfuric acid at 20° C. over one hour and then further stirred for an additional two hours. 3090 g of 98% nitric acid and 660 g of 98% sulfuric acid were further added to the resultant slurry to adjust the slurry composition to x=64.3 and y=60 in the foregoing equations. Then, the adjusted slurry was suspended with heating at 90° C. for five hours and filtered at 40° C. to obtain a cake weighing 93.0 g (31.2% yield). The cake composition was as follows:

1,5-dinitroanthraquinone: 95.2%
1,8-dinitroanthraquinone: 4.3%
others: 0.5%

COMPARISON EXAMPLE 1

The same procedures as in Example 1 were repeated except that the slurry resulting from the anthraquinone by the dinitration reaction was treated without subjecting to the heating suspension. The conditions and the results are as shown in Table 1, where 1,5-isomer cake of a low purity is obtained.

COMPARISON EXAMPLES 2–4

In these examples, heating suspension was conducted under the conditions out side of the range specified above. As can be seen from the results shown in Table 1, none of the examples can provide 1,5-dinitro isomer cake of a high purity.

COMPARISON EXAMPLES 5–6

The same procedures as in Example 6 were repeated except that anthraquinone was added over longer periods of time. The results show that the purity of the resulting 1,5-isomer cake is below 90% and high purity can not be attained even if the time for the heating suspension is increased. The conditions and the results of the experiments are also shown in Table 1.

Table 1

| Example No. | Charging weight | | | Nitration condition | | | Heat suspension condition | | | | Filtration temperature (°C.) | yield (%) | 1,5-isomer cake composition (%) | | |
|---|---|---|---|---|---|---|---|---|---|---|---|---|---|---|---|
| | anthraquinone | 98% nitric acid | 98% sulfuric acid | temperature (°C.) | anthraquinone add. time (hr) | holding time (hr) | temperature (°C.) | time (hr) | x | y | | | 1,5-isomer | 1,8-isomer | beta-isomers |
| 1 | 208 g | 2894 g | 1551 g | 40 | 1 | 2 | 80 | 6 | 44.8 | 65 | 40 | 32.8 | 95.2 | 4.7 | 0.4 |
| 2 | 208 | 4107 | 2773 | 20 | 1 | 2 | 90 | 5 | 64.7 | 60 | 40 | 30.4 | 95.9 | 3.7 | 0.4 |
| 3 | 208 | 2627 | 2017 | 40 | 1 | 2 | 80 | 2 | 40.4 | 55 | 60 | 31.9 | 91.5 | 7.7 | 0.8 |
| 4 | 208 | 2792 | 2974 | 40 | 2 | — | 80 | 2 | 59.7 | 55 | 60 | 29.2 | 94.2 | 5.3 | 0.5 |
| 5 | 208 | 4948 | 4337 | 40 | 2 | 1 | 90 | 3 | 78.5 | 52.5 | 60 | 30.7 | 93.8 | 5.6 | 0.6 |
| 6 | 20.8 kg | 366.4 kg | 297.8 kg | 40 | 0.5 | — | 80 | 0.5 | 57.5 | 54.1 | 60 | 36.2 | 94.3 | 5.1 | 0.5 |
| 7 | 20.8 kg/hr | 385.0 kg/hr | 300.5 kg/hr | 40 | 0.5 | — | 80 | 0.6 | 60.2 | 55.2 | 60 | 36.5 | 93.6 | 5.6 | 0.7 | continuous

Table 1-continued

Comparison Example

| | | | | | | | | | | | | | | | |
|---|---|---|---|---|---|---|---|---|---|---|---|---|---|---|---|
| 1 | 208 g | 2894 g | 1551 g | 40 | 1 | 2 | (without heating suspension) | | | 40 | 44.8 | 74.8 | 22.3 | 2.9 |
| 2 | 208 | 1509 | 1006 | 20 | 1 | 2 | 80 | 4 | 22.3 | 60 | 40 | 38.8 | 85.8 | 12.9 | 1.3 |
| 3 | 208 | 2676 | 2958 | 20 | 1 | 2 | 90 | 4 | 41.5 | 47.5 | 60 | 34.3 | 84.4 | 13.2 | 1.4 |
| 4 | 208 | 4135 | 5013 | 20 | 1 | 2 | 90 | 4 | 65.5 | 45.2 | 60 | 36.8 | 82.5 | 15.9 | 1.6 |
| 5 | 20.8 kg | 366.3 kg | 296.8 kg | 40 | 5.0 | — | 80 | 0.5 | 57.5 | 54.1 | 60 | 40.8 | 87.2 | 11.5 | 1.3 |
| 6 | 20.8 kg | 366.3 | 296.8 | 40 | 5.0 | — | 80 | 2.0 | 57.5 | 54.1 | 60 | 40.3 | 88.0 | 10.7 | 1.4 |

EXAMPLES 9-13

These example were conducted for demonstrating the effect of a recycling system (recycling system A) wherein grain size of 1,5-dinitroanthraquinone can be increased and the amount of waste acid be decreased, by suspending with heating the isomer mixture in a specified amount of mixed acid to isolate highly pure 1,5-dinitroanthraquinone and 1,8-dinitroanthraquinone therefrom and reusing the mother liquor again for the reaction. The conditions and the results are shown in Table 2.

A continuous type experimental apparatus for each of the steps in the recycling system A shown in FIG. 2 was employed in these examples, and substantially the same procedures as in Examples 1-7 were repeated to isolate 1,5-dinitroanthraquinone using nitric acid, sulfuric acid and a mother liquor for reuse shown in Table 2 (make up at the starting).

The resultant filtrate was charged in an evaporation vessel and nitric acid was evaporated to 30-42 mol per mol anthraquinone charged at 50°-60° C. for 1-1.5 hours of residence time to cause crystallization. Then, 1,8-dinitroanthraquinone cake was obtained after filtration, washed and dried.

A 200 hour's continuous operation in which the above filtrate was reused, showed no substantial changes in the results.

EXAMPLES 14-18

These examples were conducted for demonstrating the effect of another recycling system (recycling system B) wherein the amount of waste acid can further be reduced by reusing a mother liquor for the reaction. In this example 1,8-dinitroanthraquinone cake was separated from the filtrate in the same manner as in Examples 9-13 and then isolated from the β-isomer through crystallization. The conditions and the results are also shown in Table 2.

Employing the continuous type experimental equipment for each of the steps in the recycling system B shown in FIG. 2 and in substantially the same procedures as in Examples 9-13, 1,5- and 1,8-dinitroanthraquinone cakes were separated and then the mother liquor was subjected to evaporation until the nitric acid content therein settled to about 40-50%, based on the amoung of the nitric acid at the separation of the 1,5-isomer, to isolate the β-isomer through crystallization.

A 200 hour's continuous operation in which the above filtrate was reused showed no substantial changes in the results.

EXAMPLE 19

This example was conducted in the same procedure as in Examples 14-18 except that the recycling system was not used. The conditions and the results are also shown in Table 2.

Table 2

| | | | Charging amount (kg/hr) | | | | | | | | Reuse of mother liquor (%) | Nitration condition | |
|---|---|---|---|---|---|---|---|---|---|---|---|---|---|
| | | | | reused mother liquor | | | | | | | | | |
| Example No. | Recycle system | anthra- quinone | HNO$_3$ | H$_2$SO$_4$ | H$_2$O | dinitro- anthra- quinone | others | total | 99% nitric acid | 100% sulfuric acid | | tempera- ture (°C.) | residence time (hr) |
| 9 | A | 20.8 | 141.8 | 268.0 | 20.4 | 15.6 | 4.9 | 450.6 | 313.2 | 89.3 | 75 | 40 | 0.6 |
| 10 | A | 20.8 | 237.6 | 361.1 | 37.2 | 28.8 | 9.3 | 674.0 | 299.8 | 63.8 | 85 | 40 | 0.6 |
| 11 | A | 20.8 | 58.8 | 156.0 | 7.7 | 13.4 | 4.4 | 240.3 | 341.8 | 156.0 | 50 | 30 | 0.5 |
| 12 | A | 20.8 | 269.2 | 364.3 | 52.4 | 37.9 | 14.2 | 738.0 | 242.6 | 40.5 | 90 | 40 | 0.5 |
| 13 | A | 20.8 | 238.2 | 193.3 | 31.7 | 29.7 | 10.0 | 502.6 | 201.0 | 34.1 | 85 | 20 | 0.7 |
| 14 | B | 20.8 | 72.6 | 198.1 | 24.9 | 7.4 | 9.1 | 312.1 | 384.1 | 106.6 | 65 | 40 | 0.6 |
| 15 | B | 20.8 | 104.0 | 283.5 | 59.4 | 9.2 | 12.0 | 468.1 | 299.5 | 31.5 | 90 | 40 | 0.6 |
| 16 | B | 20.8 | 40.8 | 222.6 | 24.7 | 8.4 | 11.0 | 307.5 | 340.6 | 74.2 | 75 | 20 | 0.6 |
| 17 | B | 20.8 | 29.1 | 158.8 | 8.5 | 5.9 | 6.3 | 208.6 | 377.8 | 158.8 | 50 | 30 | 0.5 |
| 18 | B | 20.8 | 34.7 | 124.5 | 25.2 | 19.3 | 12.3 | 216.1 | 272.3 | 31.1 | 80 | 20 | 0.7 |
| 19 | — | 20.8 | (mother liquor not reused) | | | | | 404.5 | 315.0 | 0 | | 40 | 0.6 |

| | Heat suspension condition | | | Filtra- tion tempera- ture (°C.) | 1,5-isomer cake | | | | 1,8-isomer cake | | H$_2$SO$_4$ not reused in mother liquor | |
|---|---|---|---|---|---|---|---|---|---|---|---|---|
| | | | | | | composition (%) | | | | | | |
| Example No. | tempera- ture (° C.) | x | y | | yield (%) | 1,5- isomer | 1,8- isomer | beta- isomers | average grain diameter (μ) | yield (%) | beta- isomer content (%) | amount (kg/hr) | ratio to 1,5- cake |
| 9 | 80 | 69.0 | 55 | 60 | 33.8 | 95.0 | 4.6 | 0.4 | 32.3 | 40.3 | 10.2 | 89.3 | 8.8 |
| 10 | 80 | 82.2 | 55 | 60 | 32.8 | 95.0 | 4.6 | 0.4 | 39.5 | 41.3 | 10.0 | 63.8 | 6.5 |
| 11 | 80 | 60.3 | 55 | 60 | 34.5 | 94.9 | 4.7 | 0.4 | 38.7 | 39.9 | 9.3 | 156.0 | 15.1 |
| 12 | 80 | 78.5 | 55 | 60 | 35.0 | 90.0 | 9.4 | 0.6 | 39.5 | 41.9 | 15.1 | 40.5 | 3.9 |
| 13 | 60 | 67.0 | 65 | 45 | 32.5 | 94.4 | 5.0 | 0.6 | 37.5 | 38.9 | 6.3 | 34.1 | 3.5 |

Table 2-continued

| | | | | | | | | | | | | | |
|---|---|---|---|---|---|---|---|---|---|---|---|---|---|
| 14 | 80 | 59.0 | 55 | 60 | 36.6 | 93.1 | 6.2 | 0.7 | 34.5 | 34.2 | 4.5 | 106.6 | 9.8 |
| 15 | 80 | 60.8 | 55 | 60 | 35.9 | 93.8 | 5.6 | 0.6 | 37.0 | 34.1 | 3.9 | 31.5 | 2.9 |
| 16 | 80 | 57.6 | 55 | 60 | 37.0 | 92.0 | 7.2 | 0.8 | 35.5 | 36.8 | 7.5 | 74.2 | 6.7 |
| 17 | 80 | 61.5 | 55 | 60 | 35.1 | 95.5 | 4.0 | 0.5 | 31.5 | 34.5 | 3.5 | 158.8 | 15.2 |
| 18 | 60 | 45.8 | 65 | 45 | 34.5 | 92.2 | 7.2 | 0.6 | 32.0 | 36.3 | 5.6 | 31.1 | 3.0 |
| 19 | 80 | 61.0 | 55 | 60 | 36.3 | 94.6 | 4.9 | 0.5 | 24.0 | 36.0 | 8.0 | 315.0 | 29.4 |

What is claimed is:

1. In a process for preparing 1,5-dinitroanthraquinone by nitrating anthraquinone with a mixture of sulfuric and nitric acids to produce a mixed isomer product, the improvement comprising:

after the nitration reaction, heating a suspension of the mixed isomer product at a temperature from 50° to 90° C. in a liquid medium consisting essentially of sulfuric acid and nitric acid as a mixed acid in proportions defined by the area encompassed by the solid line in FIG. 1 of the drawings wherein:

$$X \text{ represents } \frac{\text{nitric acid (mol.)}}{\text{dinitroanthraquinone (mol.)}}$$

$$Y \text{ represents } \frac{\text{nitric acid (weight)}}{\text{nitric acid (weight) + sulfuric acid (weight)}} \times 100$$

and then separating the resulting crystals of 1,5-dinitroanthraquinone from the suspension at a temperature of 30° to 90° C.

2. A process in accordance with claim 1 wherein the limitations for X and Y are defined by the dashed line in FIG. 1 of the drawing.

3. A process in accordance with claim 1 wherein the proportions are defined by the area defined by the dotted lines Y and the dashed lines X in FIG. 1 of the drawings.

4. A process according to claim 1, wherein said nitration reaction is effected under conditions whereby the composition of the acid mixture satisfies the values for X and Y bounded by the solid line in FIG. 1 at the time of completion of the nitration reaction.

5. A process according to claim 1, wherein the crystals of 1,5-dinitroanthraquinone are separated at a temperature from 30° to 90° C.

6. A process according to claim 1, wherein the nitration reaction is effected by adding 1 mol part of anthraquinone to the mixed acid containing more than 35 mol parts of nitric acid continuously or intermittently over a period of not more than 2 hours.

7. A process according to claim 1, wherein 1,5-dinitroanthraquinone and 1,8-dinitroanthraquinone are successively separated from the nitration reaction mixture after heating the suspension and the remaining mother liquor is recycled to the nitration reaction.

8. A process according to claim 1, wherein 1,5-dinitroanthraquinone, 1,8-dinitroanthraquinone and β-dinitroanthraquinones are successively separated from the nitration reaction mixture after heating the suspension and the remaining mother liquor is recycled to the nitration reaction.

9. A process according to claim 1, wherein said nitration reaction is effected by using a mixed acid having a molar ratio of nitric acid:sulfuric acid of 50:50 to 65:35 and a molar ratio of nitric acid to anthraquinone of more than 35.

* * * * *